United States Patent
Ryan (10) Patent No.: US 9,610,179 B2
(45) Date of Patent: Apr. 4, 2017

(54) ATRAUMATIC STENT CROWNS

(71) Applicant: Cook Medical Technologies LLC, Bloomington, IN (US)

(72) Inventor: Michael Ryan, Limerick (IE)

(73) Assignee: Cook Medical Technologies LLC, Bloomington, IN (US)

( * ) Notice: Subject to any disclaimer, the term of this patent is extended or adjusted under 35 U.S.C. 154(b) by 467 days.

(21) Appl. No.: 13/795,341

(22) Filed: Mar. 12, 2013

(65) Prior Publication Data

US 2014/0277371 A1    Sep. 18, 2014

(51) Int. Cl.
    *A61F 2/86*    (2013.01)

(52) U.S. Cl.
    CPC ........ *A61F 2/86* (2013.01); *A61F 2250/0018* (2013.01)

(58) Field of Classification Search
    CPC .... A61F 2/86; A61F 2/07; A61F 2/915; A61F 2/95; A61F 2/90; A61F 2/91; A61F 2/82; A61F 2/89; A61F 2/88; A61F 2/885; A61F 2002/91558; A61F 2002/823; A61F 2002/075; A61F 2002/91508; A61F 2002/016; A61F 2002/91541; A61F 2002/91566; A61F 2002/91525; A61F 2002/9155; A61F 2002/91575; A61F 2250/0018; A61F 2250/0036
    See application file for complete search history.

(56) References Cited

U.S. PATENT DOCUMENTS

| | | |
|---|---|---|
| 5,084,065 A * | 1/1992 | Weldon et al. ............. 623/1.44 |
| 5,776,162 A | 7/1998 | Kleshinski |
| 5,938,697 A | 8/1999 | Killion et al. |
| 6,203,569 B1 | 3/2001 | Wijay |
| 6,325,825 B1 | 12/2001 | Kula et al. |
| 6,416,543 B1 | 7/2002 | Hilaire et al. |
| 6,616,688 B2 | 9/2003 | Von Oepen |
| 6,663,664 B1 | 12/2003 | Pacetti |
| 6,776,022 B2 | 8/2004 | Kula et al. |
| 6,840,958 B2 | 1/2005 | Nunez et al. |
| 6,994,724 B2 | 2/2006 | Schmitt |
| 7,070,617 B2 | 7/2006 | Kula et al. |
| 7,547,321 B2 | 6/2009 | Silvestri et al. |
| 7,655,037 B2 | 2/2010 | Fleming, III et al. |
| 7,815,591 B2 | 10/2010 | Levine et al. |
| 7,857,842 B2 | 12/2010 | Chuter |
| 8,016,873 B1 | 9/2011 | Drasler et al. |
| 2003/0144725 A1 * | 7/2003 | Lombardi .................. 623/1.13 |
| 2004/0098099 A1 * | 5/2004 | McCullagh et al. ......... 623/1.15 |

(Continued)

FOREIGN PATENT DOCUMENTS

WO   WO 2005/011527 A1    2/2005

OTHER PUBLICATIONS

Search Report dated Feb. 5, 2013 for co-pending PCT Patent Application No. PCT/US2012/058527.

*Primary Examiner* — Jocelin Tanner (74) *Attorney, Agent, or Firm* — Brinks Gilson & Lione (57) ABSTRACT

Methods and apparatuses of atraumatic stents with likely reduced rates of tissue perforation are provided. The stents of the invention have crowns with crown tips having apexes made of a radial force reducing material. The apexes are soft and flexible and reduce the radial force at the crown relative to the stent body allowing the crowns to collapse with greater ease compared to the central portion of the stent.

20 Claims, 3 Drawing Sheets (56) References Cited

U.S. PATENT DOCUMENTS

| | | |
|---|---|---|
| 2004/0243216 A1* | 12/2004 | Gregorich .................... 623/1.15 |
| 2005/0049682 A1* | 3/2005 | Leanna ...................... A61F 2/90 623/1.15 |
| 2005/0256563 A1 | 11/2005 | Clerc et al. |
| 2006/0100695 A1* | 5/2006 | Peacock, III ............. A61F 2/91 623/1.42 |
| 2006/0184238 A1 | 8/2006 | Kaufmann et al. |
| 2007/0150051 A1 | 6/2007 | Arnault de la Menardiere et al. |
| 2009/0036972 A1 | 2/2009 | Gale et al. |
| 2011/0054589 A1 | 3/2011 | Bashiri et al. |
| 2011/0060401 A1 | 3/2011 | Hoerstrup et al. |
| 2011/0153003 A1 | 6/2011 | Shanley et al. |
| 2011/0184507 A1* | 7/2011 | Fischer, Jr. et al. ......... 623/1.16 |
| 2012/0083871 A1* | 4/2012 | Ryan ............................ 623/1.15 |
| 2012/0158119 A1 | 6/2012 | Kitaoka et al. |
| 2012/0226342 A1 | 9/2012 | Mickley |

* cited by examiner

ATRAUMATIC STENT CROWNS

TECHNICAL FIELD

The present invention relates to medical devices and more specifically, stents having atraumatic crowns.

BACKGROUND

Stents are medical devices commonly used to maintain patency of body vessels, such as those of the vascular and gastrointestinal systems. Stents are often delivered via a minimally invasive procedure and thereafter expanded to contact and support the inner wall of the targeted vessel. In general, most stents include a tubular shaped support structure having a plurality of interstices configured to facilitate compression and expansion of the stent.

Many stents include proximal and distal flanges or flared ends to prevent stent migration subsequent to implantation. Flanges or flares are typically set to a larger expanded diameter relative to the stent central portion and may exert a higher radial force per unit area against the vessel wall, thereby securing the stent in position. One problem with these features, however, is that the flanges or flares can damage the vessel wall if they are excessively rigid. Specifically, the crowns at the end of a flange or flare can cause perforations as the luminal wall engages the stent during peristalsis. The resulting tissue perforations may be painful and can lead to more serious complications including infection, hemorrhage, and possibly death.

BRIEF SUMMARY

In a first aspect, a stent is provided, the stent including a tubular stent body and an atraumatic stent crown connected to an end of the tubular stent body, where the atraumatic stent crown comprises a circumferential row of atraumatic crown tips and the atraumatic crown tips comprise an apex made of a radial force reducing material.

In a second aspect, a method of manufacturing a stent having atraumatic stent crowns is provided. In one embodiment, an atraumatic stent crown is made by forming crown tips by connecting the ends of separate wire segments with a material that is softer and more flexible than the wire segments. In another embodiment, separate wire segments are made by cutting conventional crown tips of a stent at the apex. In another embodiment, a stent with an atraumatic crown is made from a single wire. In yet another embodiment, a stent with an atraumatic crown is made of a plurality of wires.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims. Moreover, it is understood that the figures are not necessarily drawn to scale.

DETAILED DESCRIPTION

The exemplary embodiments illustrated provide the discovery of stents with an atraumatic crown and methods of manufacturing thereof, in which the stents may have reduced rates of tissue perforation.

The present invention is not limited to those embodiments described herein, but rather, the disclosure includes all equivalents including those of different shapes, sizes, and configurations, including but not limited to, other types of stents. Although the structures and methods of the present invention will be generally described with reference to simple tubular prostheses having a single lumen, it will be understood that the structures and methods of the present invention also encompass more complex branching endoluminal prostheses.

The devices and methods may be used in any field benefiting from a stent. Additionally, the devices and methods are not limited to being used with human beings, others are contemplated, including but not limited to, animals.

Unless otherwise defined, all technical and scientific terms used herein have the same meaning as commonly understood by one of ordinary skill in the art. In case of conflict, the present document, including definitions, will control. Preferred methods and materials are described below, although apparatuses, methods, and materials similar or equivalent to those described herein can be used in practice or testing. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

The term "proximal," as used herein, refers to a direction that is generally towards a physician during a medical procedure.

The term "distal," as used herein, refers to a direction that is generally towards a target site within a patient's anatomy during a medical procedure.

The term "biocompatible," as used herein, refers to a material that is substantially non-toxic in the in vivo environment of its intended use, and that is not substantially rejected by the patient's physiological system. A biocompatible structure or material, when introduced into a majority of patients, will not cause an undesirably adverse, long-lived or escalating biological reaction or response. Such a response is distinguished from a mild, transient inflammation which typically accompanies surgery or implantation of foreign objects into a living organism.

When in a body, stents are often subjected to tortuous conditions, especially in bodily areas wherein peristaltic motion is present or when the stent is subjected to a curved orientation, such as when disposed within the colon or duodenum. When in such a position, the radial force exerted by the stent onto the surrounding tissue may cause such tissue to perforate, thereby injuring or causing death to the patient. One advantage from the embodiments disclosed herein and equivalents thereto is that the stent is able to better conform to the tissue and is better able to adapt to the tissue environment while maintaining good radial force to maintain an open pathway. Another advantage includes, but is not limited to, that the embodiments may aid in the reduction of hyperplasia in that the radial force exerted from the stent may be tailored to the surrounding tissue. Such benefits and other benefits are achievable through various apparatuses and methods described herein and equivalents thereto.

A more detailed description of the embodiments will now be given with reference to FIGS. 1A-2C. Throughout the disclosure, like reference numerals and letters refer to like elements. The present disclosure is not limited to the embodiments illustrated; to the contrary, the present disclosure specifically contemplates other embodiments not illustrated but intended to be included in the claims.

Figure 1A:
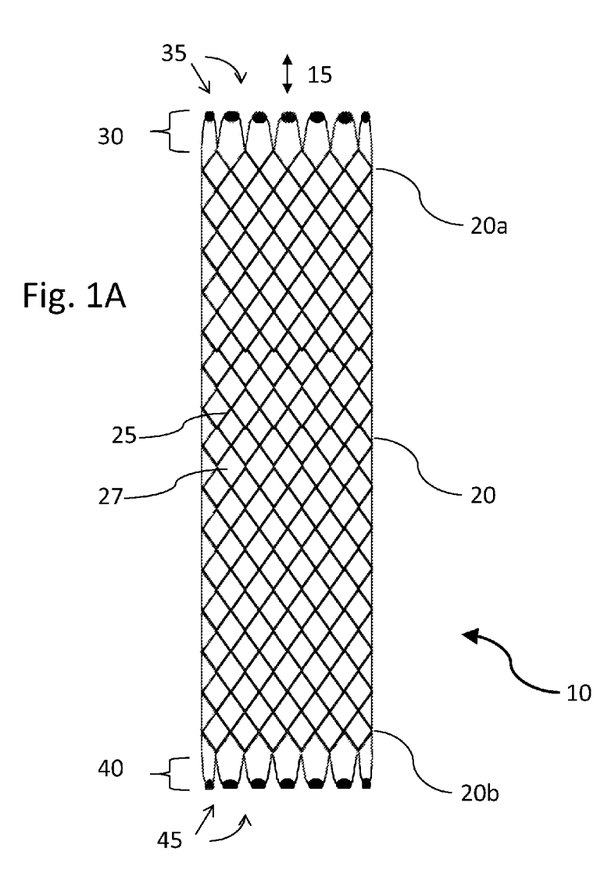
FIG. 1A illustrates a side view of an exemplary stent with atraumatic crowns.

FIG. 1A illustrates a side view of an exemplary stent 10 having atraumatic stent crowns 30 and 40. Stent 10 is composed of a tubular stent body 20 having a first end 20a, a second end 20b, a first crown 30 and a second crown 40, and a longitudinal axis in the direction of arrow 15. In certain embodiments, stent 10 is composed of a plurality of stent struts (e.g., 25) that form a plurality of stent cells 27. Stent 10 is preferably made from a shape memory alloy, such as nitinol, although other materials are contemplated, including but not limited to FeMnSi and FeNiCo(Al,Ti)Ta with or without B, $Fe_3Pt$.

An atraumatic crown has a plurality of crown tips having apexes made of a radial force reducing material. The first crown 30 comprises a first circumferential row of first crown tips 35. The second crown 40 comprises a second circumferential row of second crown tips 45. In certain embodiments, a stent according to the invention may have an atraumatic crown at one end, or on both ends as shown in FIG. 1A. For example, a stent may include a conventional crown on one end and a soft/atraumatic crown on the other. In certain embodiments, the first or second crown comprises a circumferential row of crown tips where a plurality of the crown tips have an apex made of a radial force reducing material. When a plurality of crown tips have an apex made of a radial force reducing material, other crown tips of the crown may have conventional apexes. In other embodiments, all or substantially all the crown tips have an apex made of a radial force reducing material (e.g., FIG. 1A). For example, in one embodiment each apex of a plurality of first crown tips comprises a radial force reducing connector segment that may be made of a material that is more soft and flexible than the adjacent wire segments of the first crown tips. In other embodiments, all or substantially all of the apexes of the first crown tips comprise a radial force reducing connector segment. In an alternative embodiment, each apex of a plurality of first crown tips and each apex of a plurality of second crown tips comprises a radial force reducing connector segment that may be made of a material that is more soft and flexible than the adjacent wire segments of the first and second crown tips. In yet another embodiment, all or substantially all of the apexes of the first crown tips and all or substantially all of the apexes of the second crown tips comprise a radial force reducing connector segment as described herein.

Figure 1B:
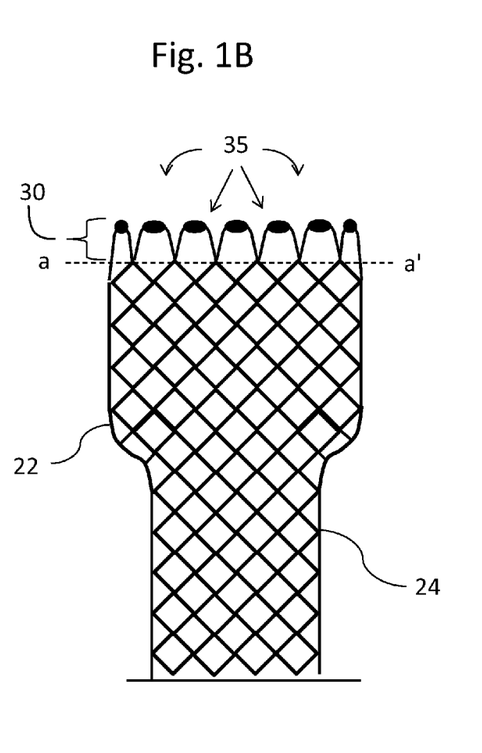
FIG. 1B illustrates a partial side view of an exemplary stent with a flanged end and a crown comprising a circumferential row of crown tips.
Figure 1C:
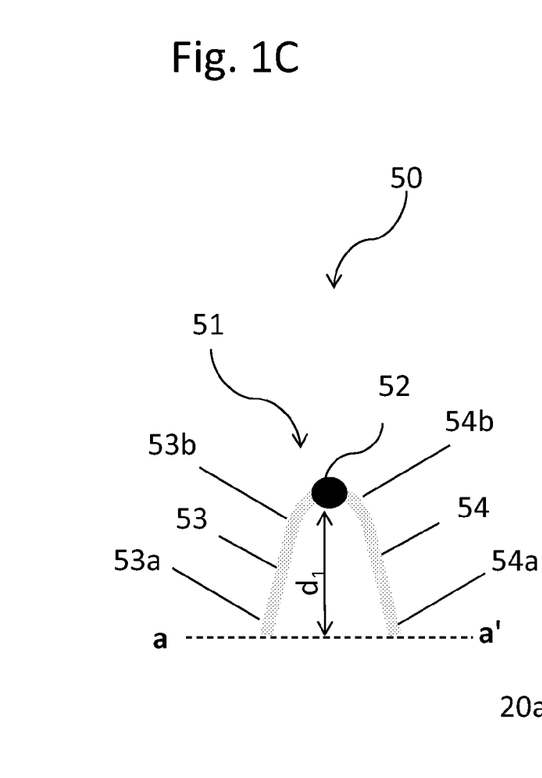
FIG. 1C illustrates a detailed side view of an exemplary single crown tip.

FIG. 1B illustrates a view of a portion of an exemplary tubular atraumatic stent with an atraumatic crown. The illustrative stent shown in FIG. 1B has a flange 22 and a central body portion 24. The exemplary atraumatic stent crown 30 comprises a circumferential row of crown tips 35. By way of example, FIG. 1C illustrates a single crown tip 50 in greater detail. Crown tip 50 comprises a first wire segment 53, a second wire segment 54, and an apex 51. The first wire segment has a proximal end 53a integrally connected to one end of the stent body. The first wire segment is also connected to apex 51 at the distal end 53b. Likewise, the second wire segment 54 has a proximal end 54a integrally connected to one end of the stent, and a distal end 54b connected to the apex 51. The connection points between proximal ends 53a and 54a and an end of the stent body is shown in FIGS. 1B, 1C, 1D, and 1E as a plane a-a' extending radially through the stent, substantially perpendicular to the longitudinal axis of the stent.

Apex 51 is made of a radial force reducing material. For example, the apex may be made of a material that is more soft and flexible than the adjacent wire segments or the stent body including, but not limited to, silicone. In the embodiment shown in FIG. 1C, apex 51 comprises a radial force reducing connector segment 52. The connector segment 52 may likewise be made of a softer and more flexible material than wire segments 53 and 54, including, for example, silicone. In FIG. 1C, the connector segment 52 is connected to the distal ends 53b and 54b.

As can be seen in the embodiment of FIG. 1A, the crown tips on the first crown 30 each have a first wire segment with proximal and distal ends, a second wire segment with proximal and distal ends, and an apex made of a radial force reducing material. As further illustrated in FIG. 1A, the crown tips on the second crown 40 each also have a first wire segment with proximal and distal ends, a second wire segment with proximal and distal ends, and an apex made of a radial force reducing material.

Figure 1D:
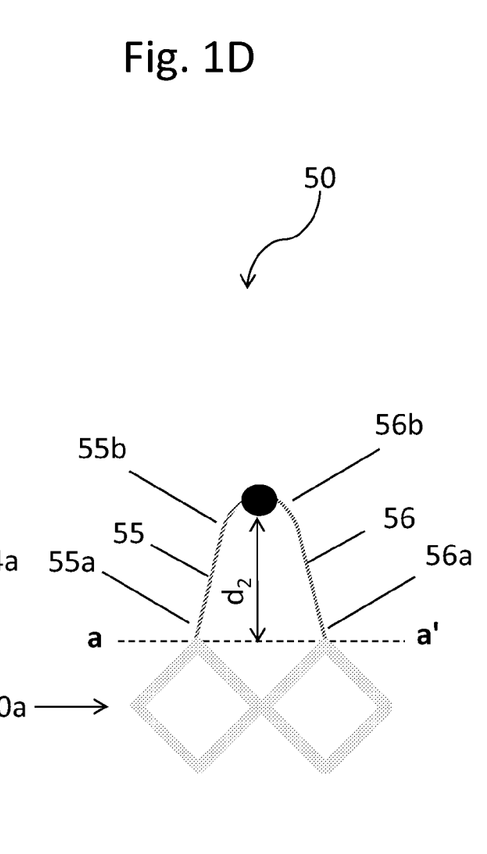
FIG. 1D illustrates a detailed side view of an exemplary single crown tip with reduced diameter wire segments relative to the stent struts.
Figure 1E:
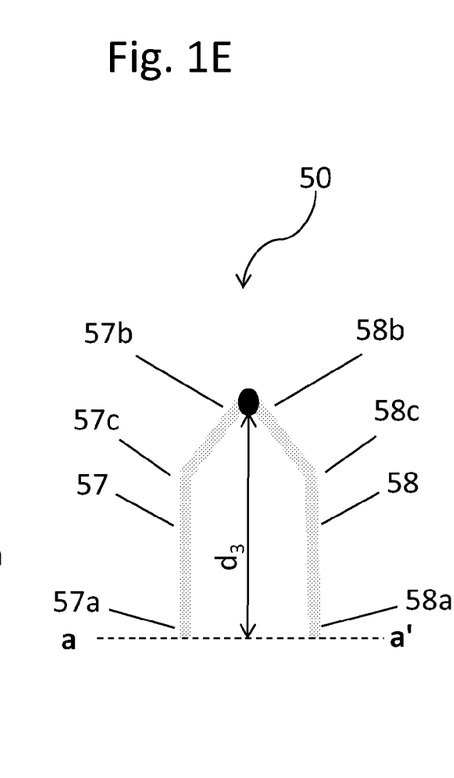
FIG. 1E illustrates a detailed side view of an alternate embodiment of an exemplary single crown tip with bent regions 57c and 58c.

The wire profile and diameter for the crown tips is not limited to that shown in FIG. 1C. For example, as illustrated in the embodiment of FIG. 1D, the first and second wire segments 55 and 56 may have a reduced diameter relative to the wire of the stent body (e.g. 20a). Likewise, the crown tip may have a variety of shapes. Thus, although the apex of the crown tip shown in FIG. 1C, and elsewhere, has a curved portion, the invention is not limited to these particular shapes. For example, the crown tip may alternatively have a "V" shape. As another example, FIG. 1E illustrates an embodiment where a first wire 57 and second wire 58 have bent regions 57c and 58c, respectively. Further variations on the shape of the crown tip that may be employed according to the invention are described in U.S. 2012/0083871, which is herein incorporated by reference in its entirety. Alternatively, in still another embodiment according to the invention, the crown tip shape of FIG. 1E may have reduced diameter wire segments as shown in FIG. 1D. In the embodiments of FIGS. 1D and 1E, and any combinations or variations thereof, the respective first and second wire segments connect to the stent body at the proximal ends 55a, 56a, 57a, 58a, and to the apex at distal ends 55b, 56b, 57b, and 58b. The connections to the stent body are as described above for proximal ends 53a and 54a. A stent may include alternative configurations of soft crown tips on each end. For example, in certain embodiments a stent may include the soft crown tips in FIG. 1C on one crown and the crown tip of FIG. 1E on the other crown.

The radial force of a crown tip depends on the flexural stiffness of the crown tip and its apex. The dominant factors for flexibility are the diameter of the wire, the profile of the wire, and the material the wire/crown tip/apex is made out of. A crown tip having an apex made of a radial force reducing material (e.g., silicone) has greater flexibility than a crown tip where the apex is made from a wire of the same material and diameter as the body of the stent or the adjacent wire segments of the crown tip (e.g., nitinol). As a consequence of the greater flexibility of the apex, the overall crown tip also has greater flexibility and therefore a reduced radial force. The flexural stiffness (K) of a component is generally defined by:

$$EI\frac{dy}{dx} = \int_0^M M(x)\,dx + C_1$$

(hereafter, "Equation 1"), where E=materials Young's modulus (Pascal); I=second moment of inertia ($m^4$); y=transverse displacement of a beam at x; and M(x)=bending moment at x. The flexural stiffness has SI units of $Pa \cdot m^4$. Young's modulus for silicone is significantly different from nitinol, therefore the flexural stiffness of a crown tip with an apex made of silicone will be significantly different compared to a crown tip made entirely of nitinol. Changing the material properties of the apexes of the crown tips from nitinol to a softer and more flexible material reduces the radial force at the crown relative to the stent body allowing the crowns to collapse with greater ease compared to the central portion of the stent.

In certain embodiments, the Young's modulus for the radial force reducing segment is about 0.001 to about 5 GPa (gigapascal). In other embodiments, the Young's modulus is about 0.001 to about 0.1 GPa. In still other embodiments, the Young's modulus is about 0.01 to about 0.1 GPa. In yet other embodiments, the Young's modulus is about 0.01 to about 0.05 GPa. In still other embodiments, the Young's modulus is about 0.5 to about 0.1 GPa. In other embodiments, the Young's modulus is about 0.2, about 0.5, about 0.8, about 1, or about 2 GPa. Suitable materials for the radial force reducing connector include, but are not limited to, various silicones, polytetrafluoroethylene, polyurethanes, polyethylenes (low or high density), polypropylenes, or nitinol having a suitably reduced profile.

When the radial force reducing connector segment is made of a silicone or polyurethane, these materials may bond directly to the adjacent wire segments without the necessity for an adhesive. Other materials such as polytetrafluoroethylene, polyethylenes, and polypropylenes may require the use of an adhesive or a primer with an adhesive to bond to the adjacent wire segments. Alternatively, these materials may be welded to the adjacent wires with heat and pressure. In the case of polytetrafluoroethylene, the radial force reducing connector segment is preferably attached to the adjacent wires using a primer and an adhesive or by welding.

The proportions (e.g., length, diameter) of the wire segments of the crown tip and the size of the radial force reducing connector may be varied to adjust the flexibility of the crown as appropriate for the particular application. For example, further flexibility can be imparted to a crown tip by reducing the wire diameter of the wire segments connected to the apex as shown in FIG. 1D. Even a small change in diameter will have a large change on flexural stiffness in the crown. Other portions of a stent according to the invention may also have a reduced diameter wire as described in U.S. application Ser. No. 13/644,255 which is herein incorporated by reference in its entirety.

The various individual crown tips on one or both ends of a stent may exert the same radial force or a different radial force. Different levels of radial force may be achieved for each individual crown tip by varying the diameter/profile of a particular wire and/or by varying the material the wire/crown tip/apex is made out of.

The crowns tips are free from the weave framework and therefore may move independently from one another in response to an external force. Thus, the crown tips may bend inward toward the luminal space or outward toward the abluminal space. The crown tips may bend anywhere along their length, depending on the force distribution. One exemplary point where the crown tips may bend includes the pivot points where the proximal ends of the first and second wire segments (e.g. 53a, 54a) connect to the stent body. One pivot point is shown in FIGS. 1C, 1D, and 1E as a plane a-a' extending radially through the stent, approximately perpendicular to the longitudinal axis of the stent. In the embodiment of FIG. 1E, the crown tips may also independently bend or flex at bent areas 57c and 58c. With reference again to FIGS. 1C, 1D, and 1E, the longitudinal distance from the crown apex to plane a-a' is shown as distance $d_1$, $d_2$, or $d_3$. The flexibility of the crowns may be further increased by increasing the length of the wire segments of the crown tips and hence the distance $d_1$, $d_2$, or $d_3$. The additional length may allow the crown tips to better adapt to changes in lumen shape, which in turn can reduce the incidence of tissue perforations and pain to a patient.

The one or more wires comprising stent embodiments and equivalents thereto are not limited to those having a circular cross-sectional profile; other profiles are contemplated, including but not limited to, a rectangular cross-section profile, square cross-sectional profile, oval cross-sectional profile, triangular cross-section profile, an irregular (or non-uniform) cross-sectional profile, or some combination thereof. Accordingly, as used herein, a "profile" of the one or more wires may be any means of defining a diameter, length, width, height, or other measurement of a wire, such as is appropriate for the specific shape of the wire whether it be a circle, oval, rectangle, square, or other shape. Thus, although some embodiments illustrate a reduced wire diameter, the embodiments and methods are not limited to circular cross-sectional profile wires; instead, they include, but are not limited to, one or more wires having any profile shape whether that cross-sectional length, height, width, or other portion be described using a term other than "diameter." Reducing the profile of the wire such that it is different from its initial wire profile may be achieved through numerous means, including but not limited to, reducing the diameter of a round wire and/or reducing the cross section of a flat wire or changing the shape of the wire. For example, it is contemplated that the shape of round wire may be altered into more rectangular shape or other desired shape. A change of the wire profile may be achieved by electropolishing, immersion into an acid, sanding/grinding, or some combination thereof.

Figure 2A:
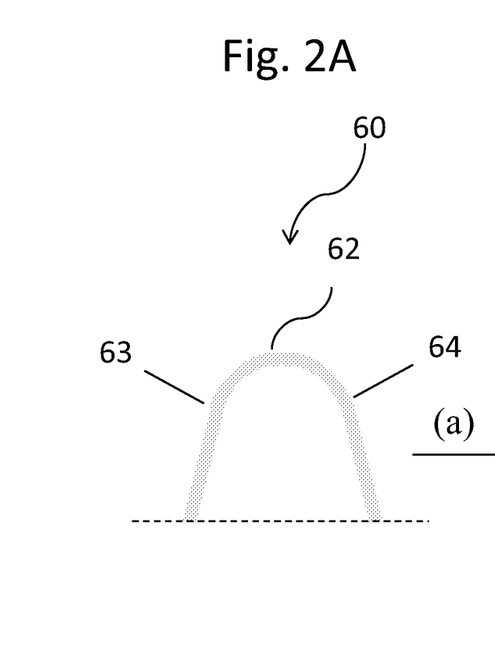
FIGS. 2A-2C illustrates one embodiment of a process for manufacturing an atraumatic stent crown tip.
Figure 2B:
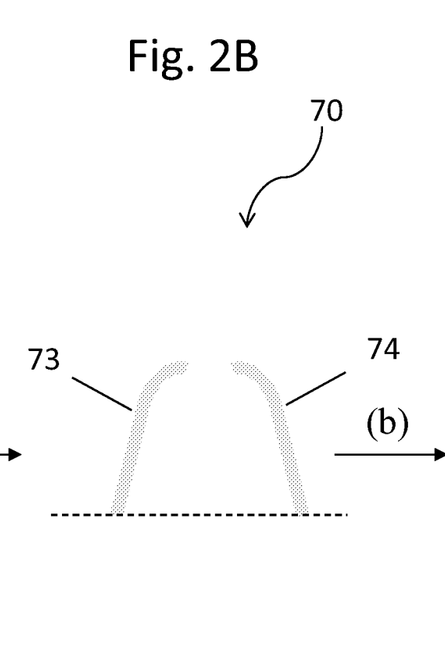
Figure 2C:
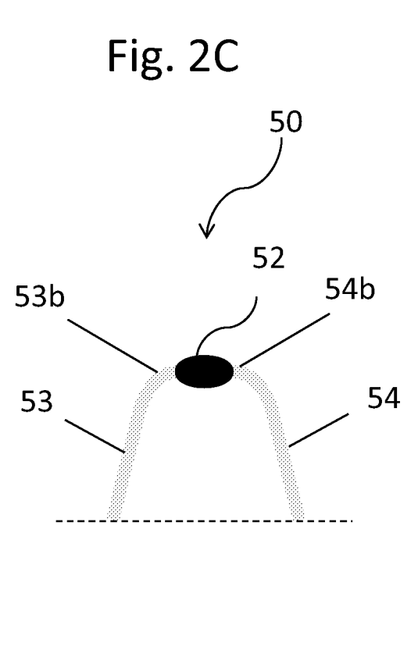

FIGS. 2A-2C illustrate one process for manufacturing an atraumatic crown tip 50. In step (a), the apex 62 of a conventional crown tip 60 is cut in one or more places to provide intermediate structure 70, which comprises first separated wire 73 and second separated wire 74 connected to an end of the stent body. The apex 62 of the conventional crown tip is made of the same or similar material as the stent body. In step (b), the apex is formed by bonding/connecting the distal ends 53b and 54b with a radial force reducing connector segment 52. The manufacture of a reduced wire diameter crown tip as in the embodiment of FIG. 1D may be accomplished by subjecting structure 70 to a wire profile reduction step to reduce the profile of wires 73 and 74, prior to bonding these wires with a radial force reducing connector. On the other hand, a reduced wire diameter crown tip as in FIG. 1D may alternatively be made by reducing the wire diameter of the conventional crown 60 prior to cutting the apex in step (a). The process illustrated in FIGS. 2A-2C is particularly suitable for the manufacture of atraumatic crowns where the conventional starting stent is formed from a single woven wire.

FIGS. 2A-2C illustrate a first step (a) where the apex 62 is cut prior to bonding the separate wire segments. However, the cutting step is not required in the case where the stent and crowns are made from multiple wires. Where multiple wires are used to fabricate a stent, the ends of two wires may simply be joined together directly as in step (b) to form a crown tip. There is no need, however, for the stent wires to have a curved portion as shown for wires 73 and 74. Straight wire segments originating from the stent body may be directly joined together at the respective ends with a radial force reducing connector.

Reduction in wire profile may be accomplished by electropolishing, crimping, swaging, grinding, and bathing one or more wires or portions thereof in acid or other chemical(s) such that the one or more profiles of the wires or portions thereof is reduced or the wire configuration is otherwise altered such that the wire is more flexible and exhibits a reduced moment of inertia. Techniques for reducing the wire profile can be found in U.S. application Ser. No. 13/644,255.

In some embodiments, a stent is covered with a membrane. The membrane covering may be applied to a stent by any suitable method as is known in the art. For example, the membrane may be applied by spraying, dipping, painting, brushing, or padding. Generally, the membrane covering or coating has a thickness ranging from about 0.0025 mm to about 2.5 mm. The thickness of the membrane may be selected, for example, by controlling the number of dips or passes made during the application process. In one exemplary embodiment, a braided stent may be dipped in silicone liquid, removed, and thereafter cured. Preferably, the coating extends over the abluminal and luminal surfaces of the filaments, and also resides in the cells or interstices defined by the filament braid pattern. In certain embodiments, the coating may be selectively applied to the luminal or abluminal surfaces of the stent structure such that the coating residing within the cells is biased to the luminal or abluminal surface of the stent structure.

In some embodiments, after the membrane has been applied to the stent structure, "soft cells" may be created by manually removing a covering, such as silicone, from the selected cells with an appropriate tool. For example, devices such as needles and forceps may be used to remove membrane material from selected cells to create a desired pattern of soft cells. In an alternative embodiment, the soft cells in the stent pattern may fabricated by covering or shielding certain cells prior to application of the membrane coating. For example a segment of shrink wrap comprising polytetrafluoroethylene may be applied to a circumferential row of cells by placing a piece of the material at the desired location and thereafter heat shrinking in place. With the selected cells shielded, the membrane material may be applied and cured, and the shrink wrap thereafter removed. This procedure may minimize or eliminate the need for manual removal of silicone from selected cells.

In some embodiments, a bioactive agent may be applied, for example, by spraying, dipping, pouring, pumping, brushing, wiping, vacuum deposition, vapor deposition, plasma deposition, electrostatic deposition, ultrasonic deposition, epitaxial growth, electrochemical deposition or any other method known to the skilled artisan.

In some embodiments, prior to applying the membrane, a stent may be polished, cleaned, and/or primed as is known in the art. A stent may be further polished, for example, with an abrasive or by electropolishing. A stent may be cleaned by inserting the stent into various solvents, degreasers, and cleansers to remove any debris, residues, or unwanted materials from the stent surfaces. Optionally, a primer coating may be applied to the stent prior to application of the membrane covering or coating. Preferably, the primer coating is dried to eliminate or remove any volatile components. Excess liquid may be blown off prior to drying the primer coating, which may be done at room temperature or at elevated temperatures under dry nitrogen or other suitable environments including an environment of reduced pressure.

In some embodiments, a stent may include a single flange, two asymmetrically shaped flanges, or may entirely lack flanges and instead have a uniform or substantially uniform lumen diameter along the entire length of the stent. In some embodiments, a stent may comprise a proximal tube portion, a distal tube portion, a central tube portion disposed between the proximal tube portion and the distal tube portion, such that the stent forms a continuous structure having a substantially uniform inner diameter and outer diameter throughout. A stent may include a uniform lumen diameter along the length of the stent but include slightly flared proximal and/or distal ends. The central body portion may smoothly transition to a flange or flare, or alternatively, may progressively step up in lumen diameter to a flange or flare.

Generally, a stent may be implanted in a vessel (e.g., esophagus, duodenum, colon, trachea, or the like) such that the central body portion engages a diseased area and the flanges or ends engage healthy tissue adjacent the diseased area. Preferably, the flanges are configured to anchor the stent at the site of implantation, thereby reducing the incidence of antegrade and retrograde migration. Preferably, the flanges are sized and shaped to accommodate the vessel or organ of implantation. For example, stents destined for lower esophageal implantation may have differently shaped and sized flanges compared to a stent designed for upper esophageal implantation. Further, the flanges may be atraumatically shaped to reduce incidence of tissue perforation and overgrowth. For example, the absolute ends of the flanges may curve or bend inward toward the stent lumen to minimize tissue damage at or near the stent ends. In certain embodiments, a stent may include other design elements configured to secure the stent at the site of implantation. For example, in certain embodiments, a stent may include anchors, hooks, or barbs that will anchor the stent to the internal wall of the targeted body lumen. In other embodiments, the stent may be sutured to the site of implantation at one or more portions of the stent structure.

In some embodiments, a stent may include one or more components configured to aid in visualization and/or adjustment of the stent during implantation, repositioning, or retrieval. For example, a stent may include one or more radiopaque markers configured to provide for fluoroscopic visualization for accurate deployment and positioning. Radiopaque markers may be affixed (e.g., by welding, gluing, suturing, or the like) at or near the ends of the stent at a cross point of the wire. In some embodiments, a stent may include four radiopaque markers with two markers affixed to a first flange and two to a second flange. Optionally, radiopacity may be added to a stent through covering (also referred to as coating) processes such as sputtering, plating, or co-drawing gold or similar heavy metals onto the stent. Radiopacity may also be included by alloy addition. Radiopaque materials and markers may be comprised of any suitable biocompatible materials, such as tungsten, tantalum, molybdenum, platinum, gold, zirconium oxide, barium salt, bismuth salt, hafnium, and/or bismuth subcarbonate. Additional methods are contemplated, including but not limited to, use of palladium or a nitinol wire with a platinum core, such as the DFT® wire available from Fort Wayne Metals, Fort Wayne, Ind.

In some embodiments, a stent may include one or more loops, lassos, or sutures on the stent structure to facilitate repositioning or removal of the stent during or after implantation. For example, a stent may include a loop at or near the proximal end of the stent. The loop material may circumscribe the flange and in certain embodiments may be wound through the absolute end cells to affix the loop to the stent. The loop may comprise any appropriate biocompatible materials, such as for example, stainless steel, suture materials or other polymeric materials such as polyethylene, ultra-high molecular weight polyethylene, polyester, nylon, or the like. Optionally, the lasso may be coated with a material, such as polytetrafluoroethylene, to reduce frictional interactions of the lasso with surrounding tissue.

In some embodiments, stents may be self-expanding, mechanically expandable, or a combination thereof. Self-expanding stents may be self-expanding under their inherent resilience or may be heat activated wherein the stent self-expands upon reaching a predetermined temperature or range of temperatures. One advantage of self-expanding stents is that traumas from external sources or natural changes in the shape of a body lumen do not permanently deform the stent. Thus, self-expanding stents are often used in vessels that are subject to changes in shape and/or changes in position, such as those of the peripheral and gastrointestinal systems. Peripheral vessels regularly change shape as the vessels experience trauma from external sources (e.g, impacts to arms, legs, etc.); and many gastrointestinal vessels naturally change shape as peristaltic motion advances food through the digestive tract.

One common procedure for implanting a self-expanding stent involves a two-step process. First, if necessary, the diseased vessel may be dilated with a balloon or other device. The stent may be loaded within a sheath that retains the stent in a compressed state for delivery to the targeted vessel. The stent may then be guided to the target anatomy via a delivery catheter and thereafter released by retracting or removing the retaining sheath. Once released from the sheath, the stent may radially expand until it contacts and presses against the vessel wall. In some procedures, self-expanding stents may be delivered with the assistance of an endoscope and/or a fluoroscope. An endoscope provides visualization of the lumen as well as working channels through which devices and instruments may be delivered to the site of implantation. A fluoroscope also provides visualization of the patient anatomy to aid in placement of an implantable device, particularly in the gastrointestinal system.

Stents according to the present disclosure may be formed by any suitable method as is known in the art. In certain embodiments, stents may be fabricated by braiding, weaving, knitting, crocheting, welding, suturing, or otherwise machining together one or more filaments or wires into a tubular frame. Such stents may be referred to as braided, woven, or mesh stents. A braided stent may be fabricated by, for example, use of a braiding mandrel having specifically designed features (e.g., grooves and detents) for creating such a stent. A variety of braiding patterns are possible, such as for example, one-under and one-over patterns or two-under and two-over patterns. The filaments (e.g., monofilaments or multifilaments) or wires may be of various cross-sectional shapes. For example, the filaments or wires may be flat in shape or may have a circular-shaped cross-section. The filaments or wires may have any suitable initial diameter, such as for example, from about 0.10 to about 0.30 mm.

In some embodiments, stents may be formed from metallic or polymeric sheets or tubular blanks. For example, a stent framework comprising a selected pattern of struts defining a plurality of cells or interstices may be fabricated by subjecting a metallic or polymeric sheet or tubular blank to laser cutting, chemical etching, high-pressure water etching, mechanical cutting, cold stamping, and/or electro discharge machining. After obtaining a sheet of cut, etched or machined material with the appropriate strut pattern, the sheet may be rolled into a tubular shape to form the stent framework. The stent framework may also be machined from a tubular blank, thereby eliminating the need for a rolling step.

In some embodiments, a stent may be made from any suitable biocompatible material(s). For example, a stent may include materials such as shape memory alloys, stainless steel, nitinol, MP35N, gold, tantalum, platinum or platinum iridium, niobium, tungsten, Iconnel® (available from Special Metals Corporation, Huntington, W. Va.), ceramic, nickel, titanium, stainless steel/titanium composite, cobalt, chromium, cobalt/chromium alloys, magnesium, aluminum, or other biocompatible metals and or composites or alloys. Examples of other materials that may be used to form stents include carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, ultra high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these.

In some embodiments, a stent may be fabricated to any suitable dimensions. A stent having a particular length and diameter may be selected based on the targeted vessel. For example, a stent designed for esophageal implantation may have a length ranging from about 5 cm to about 15 cm and a body diameter of about 10 mm to about 25 mm. Optionally, an esophageal stent may include one or more flanges or flares of about 10 mm to about 25 mm in length and about 20 mm to about 30 mm in diameter. For example, a stent designed for colon implantation may have a length ranging from about 5 cm to about 15 cm and a body diameter of about 20 mm to about 25 mm. Optionally, a colonic stent may include one or more flanges having a diameter of about 25 mm to about 35 mm.

A stent according to the present disclosure may be delivered to a body lumen using various techniques. Generally, under the aid of endoscopic and/or fluoroscopic visualization a delivery device containing the stent is advanced into the vicinity of the target anatomy. The targeted lumen may be predilated with a balloon catheter or other dilation device, if necessary. Preferably, the stent is delivered in a compressed state in a low profile delivery device. This approach may reduce the risk of tissue perforations during delivery. Once the delivery device is in place, the stent may be released from the retaining sheath or the like. In one preferred embodiment, a stent may be delivered with a controlled release system (e.g., Evolution™ Controlled-Release Stent, Cook Endoscopy Inc., Winston-Salem, N.C.). A controlled release device permits the physician to slowly release the stent from the retaining sheath and in some instances, recapture the stent to allow for repositioning. After implantation, the delivery device and any other devices (e.g., wire guides, catheters, etc.) may be removed.

From the foregoing, the discovery of methods and apparatuses of stents with likely reduced rates of tissue perforation are achieved by various methods and apparatus, including but not limited to, providing a stent with a crown comprising a plurality of crown tips, the apexes of which are made of a radial force reducing or relatively soft and flexible material. It can be seen that the embodiments illustrated and equivalents thereof as well as the methods of manufacturer may utilize machines or other resources, such as human beings, thereby reducing the time, labor, and resources required to manufacturer the embodiments. Indeed, the discovery is not limited to the embodiments illustrated herein, and the principles and methods illustrated herein may be applied and configured to any stent and equivalents.

Those of skill in the art will appreciate that embodiments not expressly illustrated herein may be practiced within the scope of the present discovery, including that features described herein for different embodiments may be combined with each other and/or with currently-known or future-developed technologies while remaining within the scope of the claims presented here. It is therefore intended that the foregoing detailed description be regarded as illustrative rather than limiting. It is understood that the following claims, including all equivalents, are intended to define the spirit and scope of this discovery. Furthermore, the advantages described above are not necessarily the only advantages of the discovery, and it is not necessarily expected that all of the described advantages will be achieved with every embodiment of the discovery.

What is claimed is:

1. A stent comprising
   (a) a tubular stent body having a first end and a second end, the tubular stent body comprising a wire; and
   (b) a first crown comprising a circumferential row of first crown tips, each first crown tip respectively comprising:
      (i) a first wire segment of the wire extending from and free from overlap with the tubular stent body, the first wire segment having a proximal end and a distal end;
      (ii) a second wire segment of the wire extending from and free from overlap with the tubular stent body, the second wire segment having a proximal end and a distal end; and
      (iii) an apex;
   wherein the proximal end of the first wire segment and the proximal end of the second wire segment are each integrally connected with the first end of the tubular stent body and the distal end of the first wire segment and the distal end of the second wire segment are connected to the apex; and
   wherein each apex of a plurality of the first crown tips comprises, respectively, a radial force reducing connector segment connecting to, and occupying a space between, the distal end of the first wire segment and the distal end of the second wire segment of the plurality of the first crown tips, the radial force reducing connector segment being made of a softer and more flexible material than the first and second wire segments such that each crown tip of the plurality of first crown tips has greater radial flexibility than an equivalent crown tip having an apex made of the same material as the first and second wire segments.

2. The stent according to claim 1 wherein the radial force reducing connector segment has a Young's modulus less than the first and second wire segments.

3. The stent according to claim 1 wherein the radial force reducing connector segment has a Young's modulus of about 0.001 to about 5 GPa.

4. The stent according to claim 1 wherein the radial force reducing connector segment is made of silicone.

5. The stent according to claim 1 wherein each apex of substantially all the first crown tips comprises, respectively, a radial force reducing connector segment connecting to, and occupying the space between, the distal end of the first wire segment and the distal end of the second wire segment of the substantially all the first crown tips, the radial force reducing connector segment being made of a softer and more flexible material than the first and second wire segments such that each crown tip of the substantially all the first crown tips has greater radial flexibility than an equivalent crown tip having an apex made of the same material as the first and second wire segments.

6. The stent according to claim 1 further comprising:
   a second crown comprising a circumferential row of second crown tips, each second crown tip respectively comprising:
      (i) a first wire segment of the wire having a proximal end and a distal end;
      (ii) a second wire segment of the wire having a proximal end and a distal end; and
      (iii) an apex;
   wherein the proximal end of the first wire segment and the proximal end of the second wire segment are each integrally connected with the second end of the tubular stent body and the distal end of the first wire segment and the distal end of the second wire segment are connected to the apex; and
   wherein each apex of a plurality of the second crown tips comprises, respectively, a radial force reducing connector segment connecting to, and occupying a space between, the distal end of the first wire segment and the distal end of the second wire segment of the plurality of the second crown tips, the radial force reducing connector segment being made of a softer and more flexible material than the first and second wire segments such that each crown tip of the plurality of second crown tips has greater radial flexibility than an equivalent crown tip having an apex made of the same material as the first and second wire segments.

7. The stent according to claim 6 wherein the radial force reducing connector segment of the plurality of first crown tips and the radial force reducing connector segment of the plurality second crown tips each has a Young's modulus less than the first and second wire segments of the first and second crown tips.

8. The stent according to claim 6 wherein the radial force reducing connector segment of the plurality of first crown tips and the radial force reducing connector segment of the plurality second crown tips each has a Young's modulus of about 0.001 to about 5 GPa.

9. The stent according to claim 6 wherein the radial force reducing connector segment of the plurality of first crown tips and the radial force reducing connector segment of the plurality second crown tips each is made of silicone.

10. The stent according to claim 6 wherein each apex of substantially all the first crown tips comprises, respectively, a radial force reducing connector segment connecting to, and occupying the space between, the distal end of the first wire segment and the distal end of the second wire segment of the substantially all the first crown tips and each apex of substantially all the second crown tips comprises, respectively, a radial force reducing connector segment connecting to, and occupying the space between, the distal end of the first wire segment and the distal end of the second wire segment of the substantially all the second crown tips, each radial force reducing connector segment being made of a softer and more flexible material than each first and second wire segments such that each crown tip of the plurality of first crown tips and each crown tip of the plurality of second crown tips has greater radial flexibility than an equivalent crown tip having an apex made of the same material as the first and second wire segments.

11. The stent according to claim 6 wherein the wire of the tubular stent body further comprises a plurality of stent struts and a plurality of the first and second wire segments of the first and second crown tips have a reduced diameter relative to the stent struts.

12. The stent according to claim 1 wherein the wire of the tubular stent body further comprises a plurality of stent struts and a plurality of the first and second wire segments have a reduced diameter relative to the stent struts.

13. The stent according to claim 12 wherein the radial force reducing connector segment is made of silicone.

14. The stent according to claim 1, wherein the wire of the body comprises a first wire and a second wire and wherein the first wire segment of the first wire and the second wire segment of the second wire and the apex form each first crown tip.

15. The stent according to claim 1, wherein the wire comprises a filament.

16. The stent according to claim 1, wherein the wire comprises a plurality of struts forming the body.

17. The stent according to claim 1, wherein the wire comprises a single wire.

18. A method of manufacturing a stent having a plurality of atraumatic crown tips, each atraumatic crown tip, respectively, comprising a first wire segment extending from and free from overlap with a tubular stent body, the first wire segment having a proximal end and a distal end; a second wire segment extending from and free from overlap with the tubular stent body, the second wire segment having a proximal end and a distal end; and an apex; wherein the proximal end of the first wire segment and the proximal end of the second wire segment are each integrally connected with a first end of a tubular stent body and the distal end of the first wire segment and the distal end of the second wire segment are connected to the apex, the apex comprising a radial force reducing connector segment connecting to, and occupying a space between, the distal end of the first wire segment and the distal end of the second wire segment of the plurality of atraumatic crown tips, the radial force reducing connector segment being made of a softer and more flexible material than the first and second wire segments such that each crown tip of the plurality of second crown tips has greater radial flexibility than an equivalent crown tip having an apex made of the same material as the first and second wire segments, the method comprising:

bonding a distal end of a first separated wire and a distal end of a second separated wire to a radial force reducing connector segment, wherein a proximal end of each of the first separated wire and the second separated wire is integrally connected with the first end of the tubular stent body.

19. The method of claim 18 further comprising:
reducing wire diameters of the first and second separated wires.

20. The method of claim 18 further comprising:
cutting an apex of a first crown tip to provide the first separated wire and the second separated wire.

* * * * *